United States Patent [19]
Ohi et al.

[11] Patent Number: 4,550,030
[45] Date of Patent: Oct. 29, 1985

[54] METHOD FOR STRENGTHENING DENTAL RESTORATIVE MATERIAL

[75] Inventors: Nobukazu Ohi, Fuchu; Koji Ohno; Hiroshi Kamohara, both of Tokyo, all of Japan

[73] Assignee: G-C Dental Industrial Corp., Tokyo, Japan

[21] Appl. No.: 650,544

[22] Filed: Sep. 14, 1984

[30] Foreign Application Priority Data

Jan. 26, 1984 [JP] Japan .................................. 59-11034

[51] Int. Cl.[4] .......................... A01N 1/02; C09K 3/00
[52] U.S. Cl. .......................................... 427/2; 106/35; 427/224; 427/376.1; 433/202.1; 433/212.1; 433/217.1
[58] Field of Search ................ 427/2, 224, 299, 376.1, 427/372.2; 433/202, 212, 217; 106/35

[56] References Cited
U.S. PATENT DOCUMENTS 4,120,729 10/1978 Smyth et al. ........................... 106/35
4,235,633 11/1980 Tomioka et al. ...................... 106/35
4,362,510 12/1982 Brauer et al. ...................... 106/35 X Primary Examiner—Michael R. Lusignan
Attorney, Agent, or Firm—Oblon, Fisher, Spivak, McClelland & Maier

[57] ABSTRACT

A method for strengthening dental restorative material is disclosed, which comprises depositing one or more inorganic salts of metals selected from rubidium, cesium, and potassium on the surface of a coated material of a dental restorative material obtained by coating and firing a dental porcelain fused to metal material. The dental restorative material is containing leucite and sodium on the surface of a dental alloy substrate, and heat treating the coated material at temperatures of 380° C. or higher but lower than the melting point of the inorganic salt and the strain temperature of the coated material. According to the method of this invention, the coated material can be strengthened with ease while maintaining its translucency and color tone, without using any special device.

7 Claims, 1 Drawing Figure

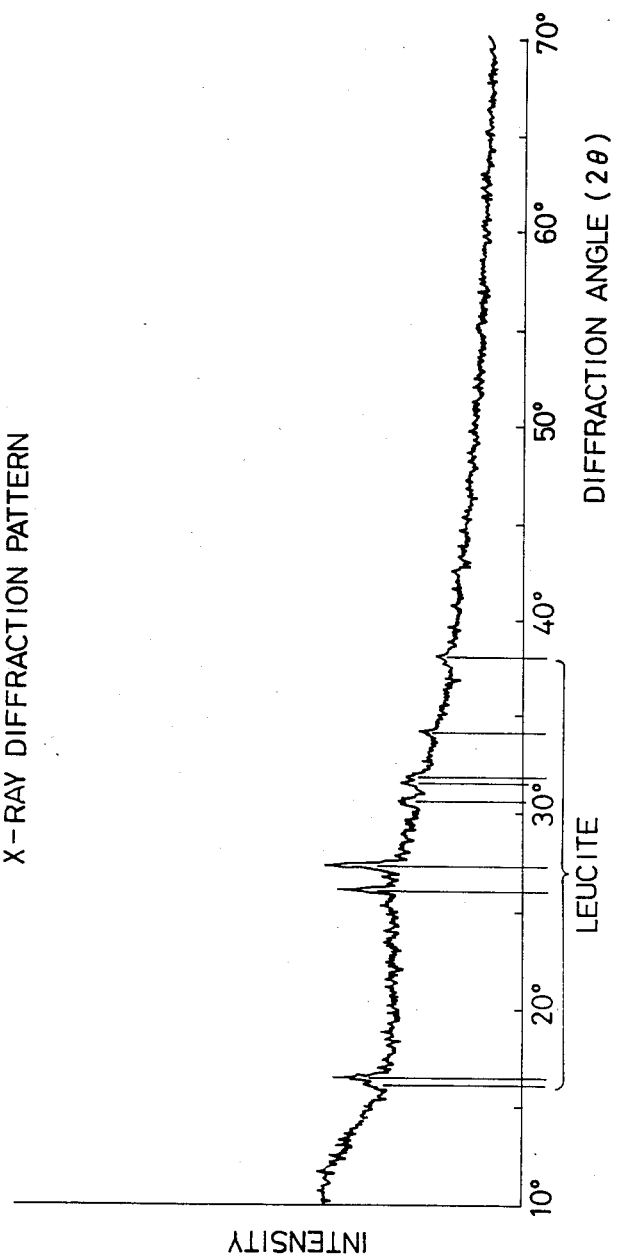

METHOD FOR STRENGTHENING DENTAL RESTORATIVE MATERIAL

FIELD OF THE INVENTION

This invention relates to a method for strengthening dental restorative material coated and fired on the surface of a dental alloy substrate. These dental restorative materials are further characterized by having dental porcelain fused a metal material.

BACKGROUND OF THE INVENTION

In dentistry, various dental restorative materials are used for restorating a deficit after medically treating a decay in a natural tooth etc. Among these are dental restorative materials prepared by coating and firing a dental alloy substrate as a coping. Such materials are prepared by a casting method, where a dental porcelain is fused to a metal material at 800° C. to 1,000° C. (the dental restorative material may hereinafter be referred to as "dental porcelain fused to metal crown"). This material is not only chemically stable but also has translucency and color tone well matched with a natural tooth and hence has been widely used.

However, when such a dental restorative material is set up and fixed in the mouth and it is applied with external forces, for example, by mastication, etc., its coating often breaks. In order to solve this problem, various attempts have been made to reduce the external forces applied to the coated material by altering its form. In order to give a natural feeling when set up in the mouth or to meet the aesthetic sense of a person who sets it up, it is desired that the strength of the material itself (the coated material) of the dental restorative material is improved to thereby prevent the breakage caused by external forces, without affecting its natural form. From this viewpoint, various modifications of the composition of the dental porcelain fused to a metal material used as a raw material of the above described coated material have been made but not without satisfactory effects. For example, when a crystal of high purity alumina is contained in a dental porcelain fused to metal material, the strength is improved, but at the same time opacity increases and the color tone, as in a natural tooth, is lost. Accordingly, the development of a method for thoroughly strengthening the coated material of the dental restorative material while maintaining translucency and color tone (as in a natural tooth), without taking an unnatural form has still been sorely required in the field of dental restoration.

In order to meet this demand, the inventors have extensively investigated and finally confirmed that when, after forming a coated material, the coated material is deposited with a specified inorganic salt of metal added thereto and then heated at a specified temperature, the coated material can be thoroughly strengthened by inorganic salt at a non-molten state.

SUMMARY OF THE INVENTION

An object of this invention is to provide a method for strengthening dental restorative material with which, after the formation of a coated material for a dental restorative material, the coated material can be strengthened with ease and safety without using any special devices.

In other words, this invention relates to a method for strengthening dental restorative material comprising depositing one or more inorganic salts of metals selected from rubidium, cesium, and potassium on the surface of a coated material of a dental restorative material obtained by coating and firing a dental porcelain fused to a metal material on the surface of a dental alloy substrate. Wherein the dental porcelain material contains leucite and sodium. The dental restorative material is then heat treated at temperature of 380° C. or higher but lower than the melting point of the inorganic salt and the strain temperature of the coated material.

BRIEF DESCRIPTION OF THE DRAWING

The FIGURE is an X-ray diffraction pattern of the dental porcelain fused to metal material used for the preparation of the coated material of the dental restorative material used in the Examples and Comparative Examples.

DETAILED DESCRIPTION OF THE INVENTION

A dental restorative material to which the method of this invention is subjected for strengthening is a dental restorative material made of a dental porcelain fused to metal crown obtained by coating and firing a dental porcelain fused to metal material on the surface of a dental alloy substrate at 800° C. to 1,000° C. According to this invention, the strengthening can be performed regardless of the form of dental restorative material, such as single crown, bridge, etc. The above described dental alloy substrate has a melting point higher than the above specified firing temperature, and in general it has a coefficient of thermal expansion of $10 \times 10^{-6}/°C.$ to $20 \times 10^{-6}/°C.$ In order that not only the coated material prepared by firing the dental porcelain fused to metal material on the surface of the dental alloy substrate have a desired color tone but also that the dental alloy substrate has a coefficient of thermal expansion substantially equal to the above described coefficient of thermal expansion, i.e., ranging from $10 \times 10^{-6}/°C.$ to $20 \times 10^{-6}/°C.$, so as to prevent the occurrence of breakage of the coated material caused by a difference in the coefficient of thermal expansion between the dental alloy substrate and the coated material during the heating or cooling step, the dental porcelain fused to the metal material is prepared such that it has a specified composition containing leucite, as explained hereunder.

The dental porcelain fused to metal material is made of, as a main raw material, potash feldspar or a mixture of potash feldspar and quartz. It is prepared by adding to this raw material an additive such as $K_2O$, $Na_2O$, $B_2O_3$, $Li_2O$, $BaO$, etc. and then melting to form a low-melting silicate glass, followed by further heat treating two or three times at lower temperatures to form leucite. The leucite is represented by the formula, $K_2O.Al_2O_3.4SiO_2$. It has a high coefficient of thermal expansion and therefore, if the content of leucite is adjusted, the coefficient of thermal expansion of the dental porcelain fused to metal material can be suited for that of the dental alloy substrate. Further, since the leucite has substantially the same refractive index as in glass, even though the leucite is formed in the glass, the translucency is never hindered. The leucite can be obtained by melting potash feldspar. If the dental porcelain fused to metal material is made only of the main raw material, the resulting porcelain material would have a higher melting point at about 1,300° C. Thus an additive such as $K_2O$, $Na_2O$, $B_2O_3$, $Li_2O$, $BaO$, etc. are added to the main raw material, the mixture is sitering at a high temperature (1,200° C. to 1,300° C.) to obtain a non-crystalline powder, and the noncrystalline powder is further heat treated two or three times at a low temperature (700° C. to 1,000° C.) to thereby deposit the leucite. The melting point of the dental porcelain fused to metal material is thus reduced to such an extent that it can be fired at the above described firing temperature (800° C. to 1,000° C.). After the additive has been added as described above, the coefficient of thermal expansion of the coated material obtained from the dental porcelain fused to metal material can be adjusted by the heat treatment. In particular, $Na_2O$ is an important additive for obtaining a coefficient of thermal expansion suited for the dental alloy substrate. In general, $Na_2O$ is present as an impurity in potash feldspar and hence, even though $Na_2O$ is not particularly added as an additive, the dental porcelain fused to metal material can generally contain $Na_2O$.

The dental restorative material containing a coated material obtained by coating and firing a dental porcelain fused to metal material containing leucite and sodium on the surface of a dental alloy substrate is strengthened in accordance with the method of this invention in the following manner. Namely, one or more inorganic salts of metals selected from rubidium, cesium, and potassium (the inorganic salt may hereinafter be referred to as "strengthening inorganic metal salt") is deposited on the surface of the coated material of the dental restorative material. The coated material is then heat treated at temperatures of 380° C. or higher but lower than the melting point of the inorganic salt and the strain temperature of the coated material (a temperature at which the viscosity is $10^{14.5}$ poises). By this heat treatment ion exchange occurs between the sodium ion in the coated material of the dental restorative material (this may be simply referred to as "coated material") and the rubidium ion, cesium ion, or potassium ion in the strengthening inorganic metal salt deposited thereon. The size of the sodium ion is 1.9 Å whereas the sizes of the potassium ion, rubidium ion, and cesium ion are 2.66 Å, 2.96 Å and 3.38 Å, respectively, the latter values being larger than the value of the sodium ion. Thus a stress generates on the surface of the coated material because of the ion exchange. The thus generated stress retains as a compressive stress even after the cooling of the coated material, whereby the strengthening of the coated material, i.e., the strengthening of the dental restorative material, is performed. Though a lithium ion also undergoes the ion exchange with the sodium ion, since its size is 1.2 ÅA (which is smaller than that of the sodium ion) it cannot generate the compressive stress. Accordingly, the lithium ion is not employable in the invention.

In the method of this invention, the heat treatment for depositing a strengthening inorganic metal salt containing an ion has the desired strengthening effect on the surface of a coated material when carried out at temperatures of 380° C. or higher. At this temperature the ion exchange can be thoroughly achieved by the heat treatment at a temperature lower than the melting point of the strengthening inorganic metal salt, i.e., in the non-molten state thereof. In the method of this invention, an organic compound is not employable as a compound containing an ion capable of such a strengthening effect because the organic compound is likely to decompose at temperatures of 380° C. or higher.

Accordingly, the strengthening inorganic metal salt which can be used in the method of this invention is an inorganic salt of rubidium, cesium, or potassium, having a melting point of 380° C. or higher. Specific examples thereof include rubidium carbonate (m.p. 837° C.), rubidium chloride (m.p. 717° C.), cesium chloride (m.p. 645° C.), potassium carbonate (m.p. 891° C.), and potassium chloride (m.p. 776° C.). Further, rubidium sulfate (m.p. 1,060° C.), cesium sulfate (m.p. 1,010° C.), potassium sulfate (m.p. 1069° C.), potassium tertiary phosphate (m.p. 1,340° C.), and potassium pyrophosphate (m.p. 1,100° C.) can also be used. But the strengthening inorganic metal salt which can be used in the method of this invention is not limited to these exemplified inorganic salts. The strengthening inorganic metal salt can be used either alone or in admixture of two or more thereof.

In depositing the strengthening inorganic metal salt on the coated material of the dental restorative material, the strengthening inorganic metal salt is dissolved or dispersed in a depositing liquid such as water or an oil. A small amount of an organic binder may be further added as an auxiliary agent for promoting the deposition, if desired, to prepare a solution or slurry (for example, 90 g of potassium tertiary phosphate is dissolved in 100 cc of water, and 1 g of gum arabic is further added thereto). The solution or slurry is sprayed or coated on the coated material in a dry thickness of 2 to 5 mm, and the resulting coated material is pre-heated for drying such that the depositing liquid does not cause rapid boiling, etc. during the heat treatment for strengthening.

The dental restorative material prepared by depositing the strengthening inorganic metal salt on the coated material is heat treated at temperatures of 380° C. or higher. With respect to the heat treatment temperature, the effect becomes greater as the temperature increases if the temperature is lower than the melting point of the strengthening inorganic metal salt. On the other hand, if the temperature is higher than the strain temperature of the coated material fired from the dental porcelain fused to metal material, though the ion exchange takes place by the heat treatment, a compressive stress is not generated on the surface of the coated material. Or even though the compression stress would be generated, since it is lightened, the remaining compression force is so weak that the strengthening cannot be thoroughly achieved. Thus the heat treatment temperature is 380° C. or higher but lower than the melting point of the strengthening inorganic metal salt and the strain temperature of the coated material. The heat treatment time is generally sufficient within the range of from 5 minutes to 60 minutes, but a time longer than 60 minutes is also acceptable. No special device is required to be used as apparatus for the heat treatment but an electric furnace generally used by a dental technician can be used.

The thus heat treated coated material is finished by cooling and if desired, washing with water or other means. There can be thus obtained a strengthened coated material in accordance with the method of this invention.

The method of this invention enables one to thoroughly strengthen a coated material by depositing thereon a strengthening inorganic metal salt containing rubidium, cesium, or potassium and having a melting point of 380° C. or higher and heat treating the coated material at temperatures of 380° C. or higher but at least lower than the melting point of the strengthening inorganic metal salt. This thereby causes ion exchange of the strengthening inorganic metal salt with a sodium ion of the coated material in the non-molten state of the strengthening inorganic metal salt. Further, the thus obtained strengthened coated material is prevented from the occurrence of dropping or movement of the strengthening inorganic metal salt deposited from the coated material upon melting and liquefying, and even a small amount of the strengthening inorganic metal salt used effectively contributes to the ion exchange, whereby it becomes possible to use a strengthening inorganic metal salt with good efficiency. Still further, the method of this invention can be accomplished by a simple heat treatment after the deposition by spraying or coating, without need of using any special device.

The invention is further explained in detail by reference to the following Examples and Comparative Examples along with the accompanying drawing.

In order that a coated material used in the Examples and Comparative Examples can be supplied for a compression testing and a bending testing, a test piece having a shape suited for these testings was prepared by the firing from a dental porcelain fused to metal material without using a dental alloy substrate. (This test piece is also referred to as "coated material" for convenience sake.)

The dental porcelain fused to metal material used contained leucite (content: 30 wt%) as shown in the Figure of intensity-diffraction angle relationship. It had a coefficient of thermal expansion of $13 \times 10^{-6}/°C$ and a strain temperature of 580° C., and the following chemical composition.

| | |
|---|---|
| $SiO_2$ | 62 wt % |
| $Al_2O_3$ | 17 wt % |
| $K_2O$ | 10 wt % |
| $Na_2O$ | 6 wt % |
| $B_2O_4$ | 4 wt % |
| others | 1 wt % |

The dental porcelain fused to metal material was mixed with water to form a slurry. The slurry was then filled in a mold for molding and fired at about 920° C., followed by correcting it into a predetermined shape. The resulting material was further fired at 940° C. to obtain a coated material having translucency and color tone as in a natural tooth. This coated material was provided for the Examples and Comparative Examples. Onto this coated material was coated a mixed slurry of a strengthening inorganic metal salt and a vegetable oil and then preheated to volatilize the vegetable oil, to thereby obtain a coated material in which the strengthening inorganic metal salt was deposited in a thickness of about 5 mm. Thereafter, a heat treatment was carried out under the respective condition, and the excessive strengthening inorganic metal salt was removed by washing with water. There was thus obtained a strengthened coated material in accordance with the method of this invention.

With respect to the thus obtained strengthened coated material, a compression testing and a bending testing were performed to obtain a diametral tensile strength and a bending strength, respectively.

EXAMPLES 1 TO 8

Onto the thus prepared columnar coated material having a diameter of 8 mm and a thickness of 4 mm was deposited each strengthening inorganic metal salt either alone or in admixture (only in Example 6), and the heat treatment was performed under the condition as shown in Table 1.

The columnar strengthened coated material was set up in a compression tester and compressed at a rate of 1 mm/min to the diameter direction until it was broken. A load applied at the breakage was measured, and the diametral tensile strength was calculated by the following equation:

$$\text{diametral tensile strength} = 2P/\pi \cdot d \cdot l)$$

wherein P is the load applied at the breakage; d is the diameter of the coated material; l is the thickness of the coated material, and $\pi$ is the circular constant.

The above described method for the measurement of the diametral tensile strength is widely used as the method for measuring the strength of brittle materials, such as glass, ceramics, and concrete, etc., which have a high strength against the compression force but a low strength against the tensile force. The results obtained are shown in Table 1. In the strengthened coated material obtained in each of the Examples, the translucency and color tone of the coated material (before the strengthening treatment) as in a natural tooth were maintained as they stood even after the strengthening treatment.

COMPARATIVE EXAMPLE 1

The diametral tensile strength of the same coated material used in Example 1 which, however, was not subjected to any treatment was measured. The results obtained are shown in Table 1.

COMPARATIVE EXAMPLES 2 AND 3

Coated materials were obtained in the same manner as in Example 1 except that the heat treatment was performed for 5 minutes at 600° C. (Comparative Example 2) and 300° C. (Comparative Example 3), respectively. Thus the diametral tensile strength was measured. The results obtained are shown in Table 1.

COMPARATIVE EXAMPLES 4 AND 5

Coated materials were obtained in the same manner as in Example 1 except that the strengthening inorganic metal salt was replaced by lithium carbonate (Comparative Example 4) and lithium tertiary phosphate (Comparative Example 5), respectively. Thus the diametral tensile strength was measured. The results obtained are shown in Table 1.

TABLE 1

| | Strengthening Inorganic Metal Salt | Heat Treatment Temperature (°C.) | Time (min) | Diametral Tensile Strength (kg/cm³) |
|---|---|---|---|---|
| Example 1 | Rubidium Sulfate | 500 | 5 | 840 |
| Example 2 | Rubidium Carbonate | 500 | 5 | 930 |
| Example 3 | Cesium Sulfate | 500 | 5 | 800 |
| Example 4 | Potassium Sulfate | 500 | 5 | 750 |
| Example 5 | Potassium Carbonate | 500 | 5 | 750 |
| Example 6 | Rubidium Sulfate (50 wt %) + Cesium Sulfate (50 wt %) | 500 | 5 | 790 |
| Example 7 | Potassium Tertiary Phosphate | 400 | 5 | 810 |
| Example 8 | Potassium Tertiary Phosphate | 500 | 5 | 900 |
| Comparative Example 1 | — | — | — | 530 |
| Comparative | Potassium Tertiary | 600 | 5 | 650 |

TABLE 1-continued

|  | Strengthening Inorganic Metal Salt | Heat Treatment Temperature (°C.) | Time (min) | Diametral Tensile Strength (kg/cm³) |
|---|---|---|---|---|
| Example 2 Comparative Example 3 | Phosphate Potassium Tertiary Phosphate | 300 | 5 | 600 |
| Comparative Example 4 | Lithium Carbonate | 500 | 5 | 490 |
| Comparative Example 5 | Lithium Tertiary Phosphate | 500 | 5 | 540 |

Table 1 demonstrates the following.

It can be understood by the comparison between Examples 1 to 8 and Comparative Example 1 that the strength of the coated materials processed in accordance with the method of this invention greatly increased as compared with that of the coated material not subjected to any treatment for strengthening. Such an effect can be produced by not only a single use of the strengthening inorganic metal salt but also a combined use of two or more thereof as in Example 6. Further, when an inorganic salt of lithium was deposited and the heat treatment was performed as in Comparative Examples 4 and 5, the strength of the coated materials was not at all improved as compared with that of the coated material not subjected to any treatment as in Comparative Example 1. Therefore, it can be understood that in order to improve the strength of coated material, the use of an inorganic salt of rubidium, cesium, or potassium is essential. Still further, as is clear from the comparison between Examples 7 and 8 and Comparative Example 1 and Comparative Examples 2 and 3, when the heat treatment temperature is higher than 580° C. which is the strain temperature of the coated material (i.e., the dental porcelain fused to metal material) or lower than 380° C., though the strength of all the coated materials was improved as compared with that in Comparative Example 1 which had no treatment performed, the degree of improvement was small and not enough for achieving the strenghening. Thus it can be understood that in order to greatly improve the strength of coated material, the heat treatment temperature must be 380° C. or higher but lower than the strain temperature of the coated material.

EXAMPLES 9 TO 11

A rectangular parallelpiped-shaped coated material having a length of 25 mm, a width of 7 mm, and a thickness of 3 mm was prepared in the manner as described above. Onto this coated material was deposited potassium tertiary phosphate as the strengthening inorganic metal salt, and the resulting coated material was heat treated at 500° C. for 5 minutes, 10 minutes, and 20 minutes, respectively.

With respect to the thus strengthened rectangular parallelpiped-shaped coated material, a bending testing was performed by means of three point bending at a span of 20 mm. Namely, the bending testing was performed by increasing the load until the coated material was broken. A load applied at the breakage was measured and the bending strength was calculated by the following equation:

bending strength $= 3P \cdot L/(2b \cdot d^2)$ wherein P is the load applied at the breakage; L is the span; b is the width; and d is the thickness.

The results obtained are shown in Table 2.

COMPARATIVE EXAMPLE 6

The same coated material as used in Example 9 which, however, was not subjected to any treatment was subjected to a bending testing in the same manner as in Example 9. The results obtained are shown in Table 2.

TABLE 2

|  | Heat Treatment Time (min) | Bending Strength (kg/cm²) |
|---|---|---|
| Example 9 | 5 | 1,600 |
| Example 10 | 10 | 1,720 |
| Example 11 | 20 | 1,600 |
| Comparative Example 6 | — | 1,130 |

In Table 2, the strengthening effect of coated material slightly varies depending upon the heat treatment time. Namely, although in the Examples the heat treatment for 10 minutes exhibited a maximum bending strength, all the Examples showed a great increase in bending strength at 470 kg/cm² or more as compared with Comparative Example 6 in which no treatment was performed. Accordingly, it is not required to precisely control the heat treatment time and actually a suitable heat treatment time can be set up over a broad range taking into account the shape, size, etc. of the dental restorative material.

The method of this invention produces effects of sufficiently strengthening a coated material of a dental restorative material while maintaining its translucency and color tone by subjecting a strengthening inorganic metal salt having a melting point of 380° C. or higher, deposited on the coated material to ion exchange in the coated material in the non-molten state thereof, without using any special device. Thus this invention can greatly contribute to the dental treatment.

While the invention has been described in detail and with reference to specific embodiments thereof, it will be apparent to one skilled in the art that various changes and modifications can be made therein whithout departing from the spirit and scope thereof.

What is claimed is:

1. A method for strengthening a dental restorative material, wherein the restorative material is obtained by coating and firing a dental porcelain fused to a metal material onto the surface of a dental alloy substrate, wherein the dental porcelain material contains leucite and sodium, said method comprising depositing at least one inorganic salt of a metal selected from rubidium, cesium, potassium or mixtures thereof on the surface of said coated material and heat treating the coated material at temperatures of 380° C. or higher, wherein said temperature is lower than the melting point of the inorganic salt and the strain temperature of the coated material.

2. A method for strengthening dental restorative material as claimed in claim 1, wherein said dental alloy substrate has a coefficient of thermal expansion of from $10 \times 10^{-6}/°C.$ to $20 \times 10^{-6}/°C.$, and said coated material coated and fired on the surface of said dental alloy substrate has a coefficient of thermal expansion of from $10 \times 10^{-6}/°C.$ to $20 \times 10^{-6}/°C.$ 3. A method for strengthening dental restorative material as claimed in claim 1, wherein said dental restorative material is heat treated for from 5 minutes to 60 minutes.

4. A method for strengthening dental restorative material as claimed in 2, wherein said dental restorative material is heat treated for from 5 minutes to 60 minutes.

5. The method of claim 1, wherein said dental porcelain comprises potash feldspar or a mixture of potash feldspar and quartz.

6. The method of claim 5, wherein said dental porcelain further comprises $K_2O$, $Na_2O$, $B_2O_3$, $Li_2O$, $BaO$ or a mixture thereof.

7. The method of claim 1, wherein said inorganic salt comprises rubidium carbonate, rubidium chloride, cesium chloride, potassium carbonate, potassium chloride, rubidium sulfate, cesium sulfate, potassium sulfate, potassium tertiary phosphate, potassium pyrophosphate or mixtures thereof.

* * * * *

UNITED STATES PATENT AND TRADEMARK OFFICE
CERTIFICATE OF CORRECTION

PATENT NO. : 4,550,030
DATED : October 29, 1985
INVENTOR(S) : NOBUKAZU OHI ET AL It is certified that error appears in the above-identified patent and that said Letters Patent is hereby corrected as shown below:

Column 3, line 50, delete "1.2 $\overset{\circ}{A}A$", and insert therefor -- 1.2 $\overset{\circ}{A}$ --.

Column 5, line 37, delete "$B_2O_4$", and insert therefor -- $B_2O_3$ --.

Column 6, line 55, Table 1, and Column 7, line 6, Table 1-continued, delete "$kg/cm^3$", and insert therefor -- $kg/cm^2$ --.

Signed and Sealed this

First Day of April 1986

[SEAL]

Attest:

DONALD J. QUIGG

Attesting Officer

Commissioner of Patents and Trademarks